United States Patent [19]

Rosen et al.

[11] Patent Number: 4,821,745
[45] Date of Patent: Apr. 18, 1989

[54] APPARATUS AND METHOD FOR OVERCOMING THE HABIT OF TOBACCO SMOKING

[76] Inventors: David I. Rosen; William E. Rosen, both of 2055 Wisteria La., Lafayette Hill, Pa. 19444

[21] Appl. No.: 31,909

[22] Filed: Mar. 30, 1987

Related U.S. Application Data

[63] Continuation-in-part of Ser. No. 797,938, Nov. 14, 1985, abandoned.

[51] Int. Cl.$^4$ ............................................. A24F 47/00
[52] U.S. Cl. ................................................. 131/270
[58] Field of Search ....................................... 131/270

[56] References Cited

U.S. PATENT DOCUMENTS 4,579,858  4/1986  Fernö .
4,597,961  7/1986  Etscorn .

FOREIGN PATENT DOCUMENTS 930668  7/1973  Canada .

OTHER PUBLICATIONS

Tabacco Alkaloids and Related Compounds, 1st ed. 1965, pp. 3–13.
Rose, et al: Transermal Administration of Nicotine (abstract).
Rose et al: Transdermal Nicotine Reduces Cigarette Craving and Nicotine Preference, Clin. Pharmacol. Ther. 10/85.
Encyclopedia of Psychoactive Drugs–Nicotine: An Old-Fashioned Addiction, pp. 34–37, 47–51.
Grunberg: Nicotine as a Psychoactive Drug: Appetite Regulation.
Grunberg: The Effects of Nicotine & Cigareete Smoking on Food Consumption and Taste Preferences; Addictive Behaviors, vol. 7, 1982.

Primary Examiner—V. Millin
Attorney, Agent, or Firm—William H. Eilberg

[57] ABSTRACT

The invention provides a method and apparatus which enables a user to reduce or eliminate the tobacco smoking habit. In one embodiment, the apparatus includes a patch of tobacco which is attached to the skin. A wetting agent, such as glycerine, alcohol, or water is placed between the skin and the patch. The patch is covered with a suitable plastic cover which holds the patch in place, and which allows body heat to accumulate in the region of the patch. A buffer, either acidic or alkaline, can be added to the wetting agent. The patch can be made by grinding tobacco, and/or tobacco by-products, forming the gound tobacco into a slurry, drying and slurry, and rolling the product into a thin sheet. The sheet can then be cut into relatively small pieces for use as a patch. The patch is believed to contain very small amounts of nicotine. Nevertheless, when the patch is held against the skin for an extended period, the user's craving for nicotine is markedly reduced. In another embodiment, a slurry of tobacco is applied directly to the skin. A device is disclosed which delivers the tobacco continuously to the user, and which can be refilled without removing it from the skin. The latter device includes a sponge which is saturated with the tobacco mixture. The saturated sponge is held directly against the skin of the user, for an extended period.

22 Claims, 1 Drawing Sheet

APPARATUS AND METHOD FOR OVERCOMING THE HABIT OF TOBACCO SMOKING

CROSS-REFERENCE TO PRIOR APPLICATION

This is a continuation-in-part of U.S. patent application Ser. No. 797,938, filed Nov. 14, 1985 now abandoned.

BACKGROUND OF THE INVENTION

This invention discloses an apparatus and method of reducing or eliminating the habit of tobacco smoking.

When nicotine is obtained from tobacco, as by chewing, sniffing, or smoking, the amount of nicotine absorbed into the body generally does not build up to a harmful dose, but produces certain pleasurable effects. These effects frequently lead to habitual use of tobacco.

One of the most common means of ingesting nicotine is by smoking tobacco. When the tobacco in a conventional cigarette is ignited, the combustion of the processed tobacco leaves, within the cigarette, releases nicotine vapor. As the user sucks or inhales air through the tobacco, the nicotine vapor is drawn through the cigarette and into the user's mouth and lungs.

The relative mildness of a tobacco cigarette, as compared to a pipe or cigar, permits a user to draw the smoke from the burning cigarette directly into the lungs. The nicotine vapor in the tobacco smoke is rapidly assimilated into the bloodstream, from the lungs, so that the effects of the nicotine are quickly felt.

Smoking of tobacco is known to be harmful in many ways. Of primary concern are the serious health hazards resulting from smoking combustible tobacco. Although the nicotine in tobacco is not believed to cause permanent harm to the human body, many of the other components in tobacco smoke are known to be unhealthful. Some of these components are known carcinogens. A table which lists some of the harmful components in tobacco smoke is found in "Tobacco and Tobacco Smoke: Studies in Experimental Carcinogenesis", by Ernest L. Wynder and Dietrich Hoffman of the Slaon-Kettering Institute for Cancer Research (1967), pages 496–501. The latter publication is hereby incorporated by reference herein.

Furthermore, smoking of combustible tobacco is a fire hazard. Burning cigarettes, which are carelessly discarded, have caused many fires, both within buildings and in natural environments. Moreover, smoking causes substantial economic losses, including significant damage to business and personal property resulting from burns in clothing, carpeting, furniture, etc., caused by stray ashes from cigarettes. Tobacco smoking is also annoying and harmful to non-smokers exposed to the smoke.

Because of the undesirable effects of tobacco smoking, many attempts have been made to provide acceptable substitutes for smoking, or to eliminate or reduce its harmful effects. Tobacco concentrates, for example, have been processed into tablets which may be sucked or chewed in the mouth of the user, the nicotine being absorbed into the user's body through the lining of the mouth.

Another proposed substitute for smoking combustible tobacco has been to heat tobacco without burning it. Processed tobacco releases nicotine vapor when it is heated to a temperature lower than its ignition point. Thus, a smoker might draw air through such heated tobacco, and obtain the desired nicotine, but without also ingesting the more harmful products of tobacco combustion. However, the source of heat in such devices has generally been a second, isolated portion of tobacco, which is burned conventionally. Although the burning tobacco is isolated from the tobacco which is not burned, the by-products of the burning tobacco are still released into the air, causing some of the same health risks as conventional smoking. Also, whenever tobacco is burned, the fire hazard is always present.

In another alternative device of the prior art, tobacco is heated by various pyrophorous materials, mixed with the tobacco. Such materials react with oxygen to produce sufficient heat to cause the tobacco to release nicotine vapor. With this device, however, the by-products of the reaction, which occurs within the tobacco mix, will also tend to be inhaled through the device, by the user. Such devices may therefore harm the health of the user. Moreover, these devices tend to be relatively complex and expensive to manufacture.

Other smoking substitutes have been developed, including devices containing materials which simulate the taste and aroma of tobacco, or which release additional aromatic vapors. In one such device, such materials are micro-encapsulated within a cigarette-like structure. The desired vapors are released by squeezing or crushing the device.

The present invention is a device which is easy to use, easy to manufacture, and which is not a health or fire hazard to the user, or to persons in the environment. The invention reduces or eliminates the user's craving for nicotine, even among the most habituated smokers.

SUMMARY OF THE INVENTION

In one embodiment of the invention, a patch of tobacco is placed on the user's skin, preferably on the arm, for a period of time. The patch can be made by grinding tobacco, and/or tobacco by-products, mixing the ground material with a suitable medium to form a slurry, and forming the mixture into a sheet. The mixture can be formed into a sheet with a conventional papermaking apparatus. Such apparatus includes means for heating the sheet, to vaporize any residual liquid in the material. The result is a thin sheet of tobacco which can be cut to form small patches.

When the above-described patch is applied to the skin of the user, a wetting agent, such as glycerine, alcohol, or water, is placed between the skin and the patch. The patch is covered with a suitable material, such as plastic, which holds the patch in place, and which conserves body heat in the region of the patch. The patch, which may be about one or two inches square, is held against the skin for several hours. When the patch is in place for an extended period, even a very habituated smoker will experience a reduction or elimination of the craving for nicotine. It has also been found that the patch acts as an appetite suppressant.

The operation of the patch may be improved by the addition of a buffer to the wetting agent. Such a buffer can be acidic, such as citric acid, or alkaline, such as sodium bicarbonate. However, the invention will work without the buffer.

In another embodiment, a tobacco slurry is formed and applied directly to the skin. The slurry may also be administered by saturating a sponge material and holding that material against the skin. The invention includes a device which holds the sponge against the skin, and which permits the sponge to be refilled with more slurry without removing the sponge.

It is therefore an object of the invention to provide a device for reducing or eliminating the smoking habit.

It is another object of the invention to reduce or eliminate the habit of smoking tobacco, without causing health or fire hazards, and without causing other undesirable effects.

It is another object of the invention to provide a device for eliminating the smoking habit, the device being simple to manufacture, and simple to use.

It is another object of the invention to provide a method for reducing or eliminating a user's craving for nicotine.

It is another object of the invention to provide a method and apparatus as described above, wherein the craving for nicotine is reduced or eliminated bhy an apparatus which does not itself contain significant amounts of nicotine.

It is another object of the invention to provide a device for the continuous administration of tobacco to the skin, which device can be refilled without removal from the skin.

Other objects and advantages of the invention will be apparent to persons skilled in the art, from a reading of the following brief description of the drawing, the detailed description of the invention, and the appended claims.

DETAILED DESCRIPTION OF THE INVENTION

In one embodiment of the present invention, a patch of tobacco is held against the skin of a smoker for three or more hours. A wetting agent is placed between the patch and the skin, and a suitable covering means is placed over the patch, to hold the patch in place.

The patch itself can be made of tobacco, and/or tobacco by-products, such as the stems of the tobacco plant. Such by-products are those which are the residue of conventional tobacco processing. About 20% of conventional cigarette tobacco is such residue. The patch can be made of tobacco of any kind, including tobacco used for cigars, cigarettes, or for chewing, or any mixture of the foregoing. Also, one can use unprocessed tobacco leaves directly.

The tobacco and/or tobacco by-products can be ground together into a powder, and combined with a suitable medium, to form a slurry. The slurry is transformed into a paper-like product, by conventional papermaking machinery, or by any other equivalent means. This transformation includes rolling the product into a thin sheet, and heating the product to drive off substantially all its residual moisture. Several layers of the tobacco sheet may be combined to form a patch of increased thickness, and increased tobacco content.

Figure 1:
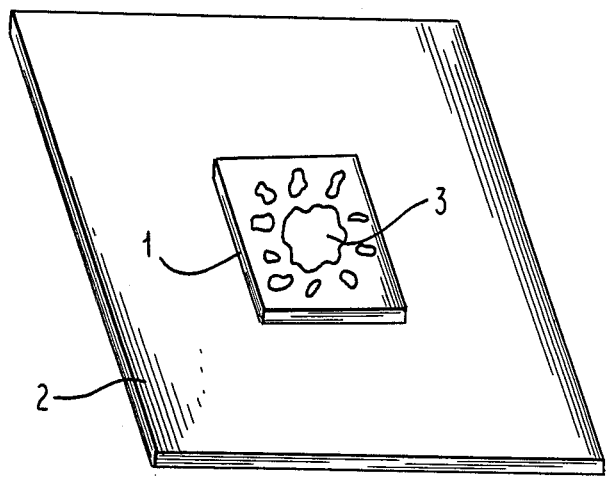
FIG. 1 is a schematic drawing showing the tobacco patch, the wetting agent, and the plastic cover, according to the present invention.

FIG. 1 shows the major components of the first embodiment of the invention described above. Tobacco patch 1 has wetting agent 3 disposed thereon. The side of the patch which has the wetting agent is ready to be applied to the arm of a user. Cover 2, which may be a plastic film, is disposed on the other side of the patch, and covers the patch when the latter is applied to the skin.

The patch can have an area of approximately 1–4 square inches, but this range is not critical, and larger patches can be used. It is preferred that the patch be small enough to fit conveniently over a small area of the user's arm. The patch can be applied to any area of the skin, but the arm is generally the most convenient location.

The wetting agent can be any of various substances such as glycerine, alcohol, or water, or combinations of these. Other wetting agents are possible. The wetting agent may be applied first to the patch, or to the skin, or both, before the patch is applied to the skin. The wetting agent is believed necessary to facilitate the migration of chemicals, from the patch, into the skin. If the patch is totally dry, there will be no such migration.

The cover can be made of various materials. It is preferred that the cover be constructed so as to maximize the retention of body heat at the patch, as it is believed that heat is also a factor in the operation of the patch.

When a user holds the patch over the skin for several hours, preferably three or more hours, the user begins to experience the sensation associated with nicotine. It may be necessary to replace the patch with a fresh patch after a day or so. After the patch has been worn for several days, the user loses almost all craving for nicotine. Even after the patch is removed, it is found that most users have permanently lost their craving for nicotine. The patch also appears to act as an appetite suppressant.

The precise mechanism by which the present invention works is not understood, but it is believed that some residual nicotine in the tobacco patch combines with other substances in the patch, and migrates into the body, through the skin, with the aid of the wetting agent, and under the influence of the body heat which is held in by the cover. The invention produces better results than the direct application of nicotine. This invention is not to be considered limited by the above hypothesis concerning the mchanism by which the invention works.

The invention can work with only the patch, the wetting agent, and the cover. However, it has been found that the invention will work more efficiently if a buffer is added to the wetting agent. Such a buffer can be either acidic or alkaline. Different kinds of tobacco have different levels of pH; the buffer should be chosen so that its pH approximates that of the tobacco. Examples of buffers that have been used include citric acid and sodium bicarbonate.

In an alternative embodiment, the tobacco is not formed into a patch, but, instead, finely ground tobacco is added to a suitable medium, to form a slurry, and then applied directly to the skin. The medium for forming the slurry can be a cream, an oil, alcohol, propylene glycol, glycerine, petroleum jelly, water, gelatin, gura gum, or other substance, or any combination of the above. The tobacco is preferably ground to a fine mesh, of the order of 200 mesh or better. The quantity of the medium should be such as to form a slurry having a viscosity similar to that of toothpaste, or thick liquid soap. A preservative, such as any food preservative, can be added to the slurry.

It is also possible to use tobacco extract, as a slurry-forming medium, but this alternative is not preferred because it is more expensive.

The slurry described above mixture can be wrapped by another material, as described below, or it can be left unwrapped.

Figure 2:
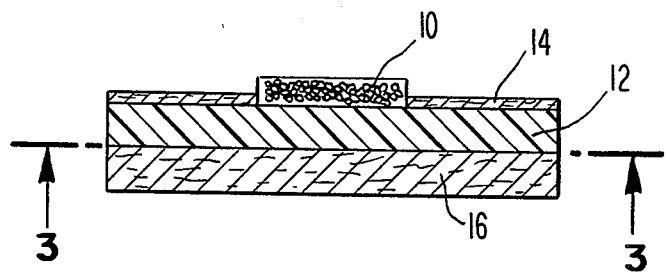
FIG. 2 is a cross-sectional view of another embodiment of the invention, wherein the tobacco is administered through a piece of foam.
Figure 3:
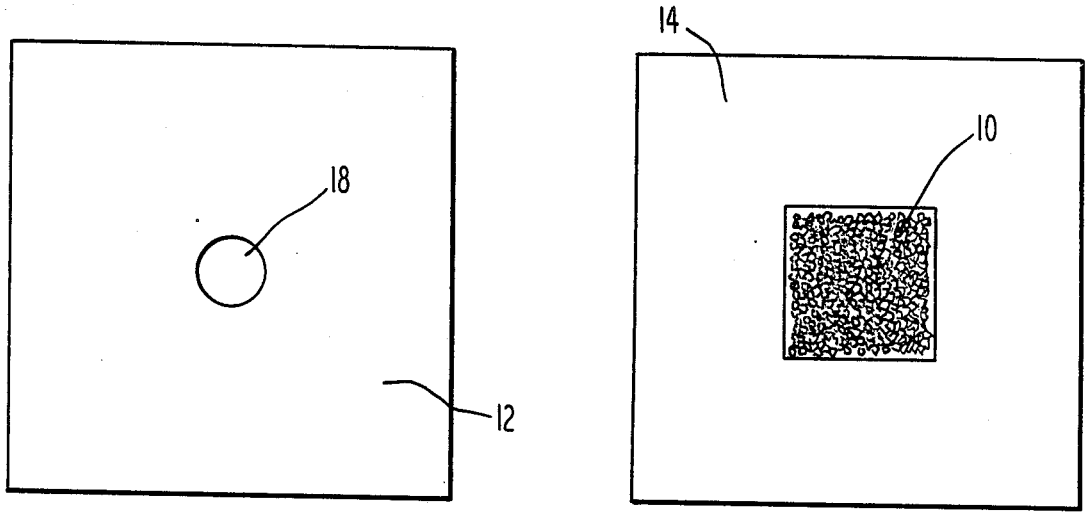
FIG. 3 is another cross-sectional view of the second embodiment, taken along the line 3—3 of FIG. 2.
Figure 4:
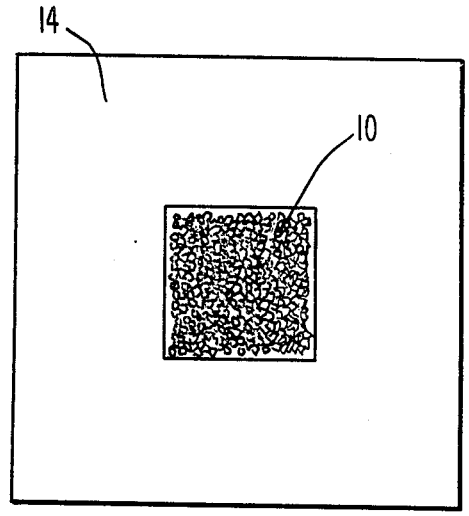
FIG. 4 is a top view of the device shown in FIG. 2.

FIGS. 2–4 show a device which can be used to deliver the tobacco to the skin, in the alternative embodiment. The device shown includes a sponge 10, made of a foam, or other absorbent material. The sponge is intended to be saturated with the tobacco mixture, and to rest upon the skin for an extended period.

Sponge 10 is attached to carrier 12, which can be a sheet of flexible material. Carrier 12 is provided with an adhesive on the side facing the sponge. A layer 14 of paper, or other thin material, covers that portion of the surface of carrier 12 which is not covered by the sponge. Cover 16 is attached to the carrier, also preferably by adhesive means.

Carrier 12 has hole 18, as shown in FIG. 3. When cover 16 is removed from carrier 12, the hole is exposed, and it is possible to apply the tobacco slurry, through the hole, to the sponge. The sponge absorbs the slurry, and the slurry permeates the sponge, and also contacts the skin of the user.

The device of FIGS. 2–4 can be applied to the skin by first removing layer 14, to expose the adhesive on carrier 12, and by pressing the carrier firmly against the skin. The tobacco slurry may be added to the sponge as described above. It is not necessary to remove the device from the skin to refill the sponge. One can simply peel off the cover, apply the slurry through the hole, and then replace the cover.

The cover need not be the same size as the carrier, but it is preferred that it be large enough to cover hole 18. Also, the hole can assume other shapes, and could also assume the form of a slit. Moreover, the hole or slit can be made to extend part or all of the way through the sponge.

In either embodiment, the tobacco can be mixed with fillers, such that the concentration of tobacco in the patch, or in the finely ground material which is added to a medium, can vary considerably. The concentration of tobacco can range from 1% to 100%.

As in the first embodiment, the tobacco in the second embodiment may be prepared with or without buffers. It is believed that a buffer is less important in the second embodiment.

The second embodiment appears to be more efficient than the first embodiment in creating the desired effects. This may be because the tobacco is already mixed into a semi-liquid. Also, the role of body heat appears to be less important in the second embodiment.

It is important to stress that the patch is made of tobacco, not nicotine. The invention is thus unlike the method disclosed in the article by J. E. Rose et al, entitled "Transdermal nicotine reduces cigarette craving and nicotine preference", Clin. Pharmacol. Ther., October, 1985, vol. 38, No. 4, pp. 450–6. The latter article describes the application of nicotine to the skin, not tobacco.

The results achieved by the present invention are surprising because the process of manufacturing the tobacco patch is believed to remove virtually all of the nicotine in the patch. Nicotine is vaporized when heated, and much heat is applied when the tobacco is pressed into a sheet. The patch is therefore made from a substance which is expected to contain little or no nicotine. Nevertheless, the small amount of nicotine which remains in the patch, after processing, somehow combines with the other substances in the tobacco, in a manner which is not understood, to produce the result described.

The same comment is true for the alternative embodiment, i.e. the direct application of tobacco slurry. The nicotine content in the slurry is also very small, since it is tobacco, not nicotine, which is used to form the slurry.

Not only is the present invention more effective than any of the devices and methods of the known prior art, but it is also inexpensive and easy to use. As explained above, at least some of the patch may be made from what is considered waste material, i.e. the tobacco by-products which are discarded during the processing of tobacco.

While the invention has been described with respect to particular embodiments, the invention should not be deemed limited by these examples. Tobacco can be provided in many forms, and, as stated above, it can be combined with many different media. The precise means for delivery of the tobacco can be varied. Many substances can be substituted for the sponge and covers described above. It is understood that the invention can thus be modified in many ways, and that such modifications are within the spirit and scope of the following claims.

What is claimed is:

1. Apparatus for enabling a smoker to reduce the smoking habit, comprising a patch of tobacco, the patch being adapted to be laid over an area of the skin of the user, a wetting agent, and a covering means, the wetting agent being disposed between the skin and the patch.

2. The apparatus of claim 1, wherein the patch comprises a dry sheet of material including ground tobacco.

3. The apparatus of claim 2, wherein the concentration of tobacco, in the patch, is less than 100%.

4. The apparatus of claim 1, wherein the wetting agent is selected from the group consisting of glycerine, alcohol, and water.

5. The apparatus of claim 1, wherein the covering means is constructed to retain body heat of the user, at the region of the patch.

6. The apparatus of claim 1, wherein the wetting agent includes a buffer.

7. The apparatus of claim 6, wherein the buffer is acidic.

8. The apparatus of claim 6, wherein the buffer is alkaline.

9. A method of reducing a user's craving for nicotine, comprising the steps of:
   (a) wetting an area of the skin of the user,
   (b) placing a patch of tobacco over the wetted area, the patch being made of ground tobacco and tobacco by-products, formed into a dried sheet,
   (c) covering the patch with a means for holding the patch in place, and
   (d) maintaining the patch in place for at least three hours.

10. A method of reducing a user's craving for nicotine, comprising the steps of mixing tobacco with a slurry-forming medium, and applying the mixture to the external portion of the skin of the user.

11. The method of claim 10, further comprising the step of covering the portion of the skin of the user which contains the mixture, and holding the mixture in place for at least three hours.

12. Apparatus for enabling a smoker to reduce the smoking habit, comprising:
(a) sponge means for holding a quantity of a tobacco-containing slurry,
(b) flexible carrier means, the sponge means being attached to the carrier means, the carrier means having a hole whereby the slurry can be applied, through the carrier means to the sponge means, and
(c) covering means, adapted to be laid onto the carrier means and to cover the hole.

13. The apparatus of claim 12, wherein the carrier means includes an adhesive, and wherein the apparatus further comprises a layer of thin material, the layer covering those portions of the carrier means not covered by the sponge means, the layer being easily removable from the carrier means.

14. The apparatus of claim 13, wherein the covering means is adhesively affixed to the carrier means, the covering means being freely removable and reattachable to the carrier means.

15. Apparatus for enabling a smoker to reduce the smoking habit, comprising sponge means for holding a quantity of a tobacco-containing slurry and a flexible carrier means, the sponge means being attached to the carrier means, the carrier means having an opening through which the slurry can be applied to the sponge means.

16. A method of reducing or eliminating a tobacco smoking habit, comprising the steps of:
(a) mixing tobacco with a medium to form a slurry,
(b) applying the slurry to a sponge means,
(c) holding the sponge means against the skin for at least three hours.

17. The method of claim 16, wherein the slurry-applying step is followed by the step of covering the sponge means with a layer of material, and holding said material against the skin.

18. The method of claim 16, further comprising the step of periodically replenishing the sponge means with more of the slurry, when the quantity of slurry in the sponge means has decreased.

19. The method of claim 16, wherein the medium is selected from one or more of the group consisting of a cream, an oil, alcohol, propylene glycol, glycerine, petroleum jelly, water, gelatin, gura gum, and tobacco extract.

20. A method of reducing a user's craving for nicotine, comprising the steps of mixing tobacco with a slurry-forming medium, applying the mixture to the skin of the user, covering the portion of the skin of the user which contains the mixture, and holding the mixture in place for at least three hours.

21. The method of claim 10, wherein the slurry is applied to an external limb of the user's body.

22. The method of claim 21, wherein the slurry is applied to the user's arm.

* * * * *